(12) United States Patent
Dwivedi et al.

(10) Patent No.: US 9,714,225 B2
(45) Date of Patent: Jul. 25, 2017

(54) PROCESSES FOR THE PREPARATION OF LORCASERIN

(71) Applicant: CADILA HEALTHCARE LIMITED, Ahmedabad, Gujarat (IN)

(72) Inventors: Shriprakash Dhar Dwivedi, Gujarat (IN); Jayprakash Ajitsingh Parihar, Gujarat (IN); Alpeshkumar Pravinchandra Shah, Gujarat (IN); Samir Rameshbhai Gajjar, Gujarat (IN); Brij Khera, Gujarat (IN)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 15/035,876

(22) PCT Filed: Nov. 13, 2014

(86) PCT No.: PCT/IN2014/000718
§ 371 (c)(1),
(2) Date: May 11, 2016

(87) PCT Pub. No.: WO2015/102017
PCT Pub. Date: Jul. 9, 2015

(65) Prior Publication Data
US 2016/0280658 A1    Sep. 29, 2016

(30) Foreign Application Priority Data
Nov. 13, 2013    (IN) .......................... 3565/MUM/2013

(51) Int. Cl.
*A61K 31/55*    (2006.01)
*C07D 223/16*    (2006.01)

(52) U.S. Cl.
CPC .................................. *C07D 223/16* (2013.01)

(58) Field of Classification Search
CPC .............................. A61K 31/55; C07D 223/16
USPC ...................................... 514/217.01; 540/594
See application file for complete search history.

(56) References Cited

U.S. PATENT DOCUMENTS 8,168,624 B2 * 5/2012 Agarwal .............. C07D 223/16
514/217.01
8,299,241 B2 * 10/2012 Gharbaoui ............ C07C 213/08
540/594

* cited by examiner

*Primary Examiner* — Brenda Coleman
(74) *Attorney, Agent, or Firm* — Ladas & Parry LLP

(57) ABSTRACT

The present invention relates to stable crystalline Form I of lorcaserin hydrochloride of Formula (IA) and processes for its preparation. The invention also relates to processes for the preparation of lorcaserin and pharmaceutically acceptable salts, solvates and hydrates thereof.

20 Claims, 3 Drawing Sheets

PROCESSES FOR THE PREPARATION OF LORCASERIN

RELATED APPLICATION

Figure 1:
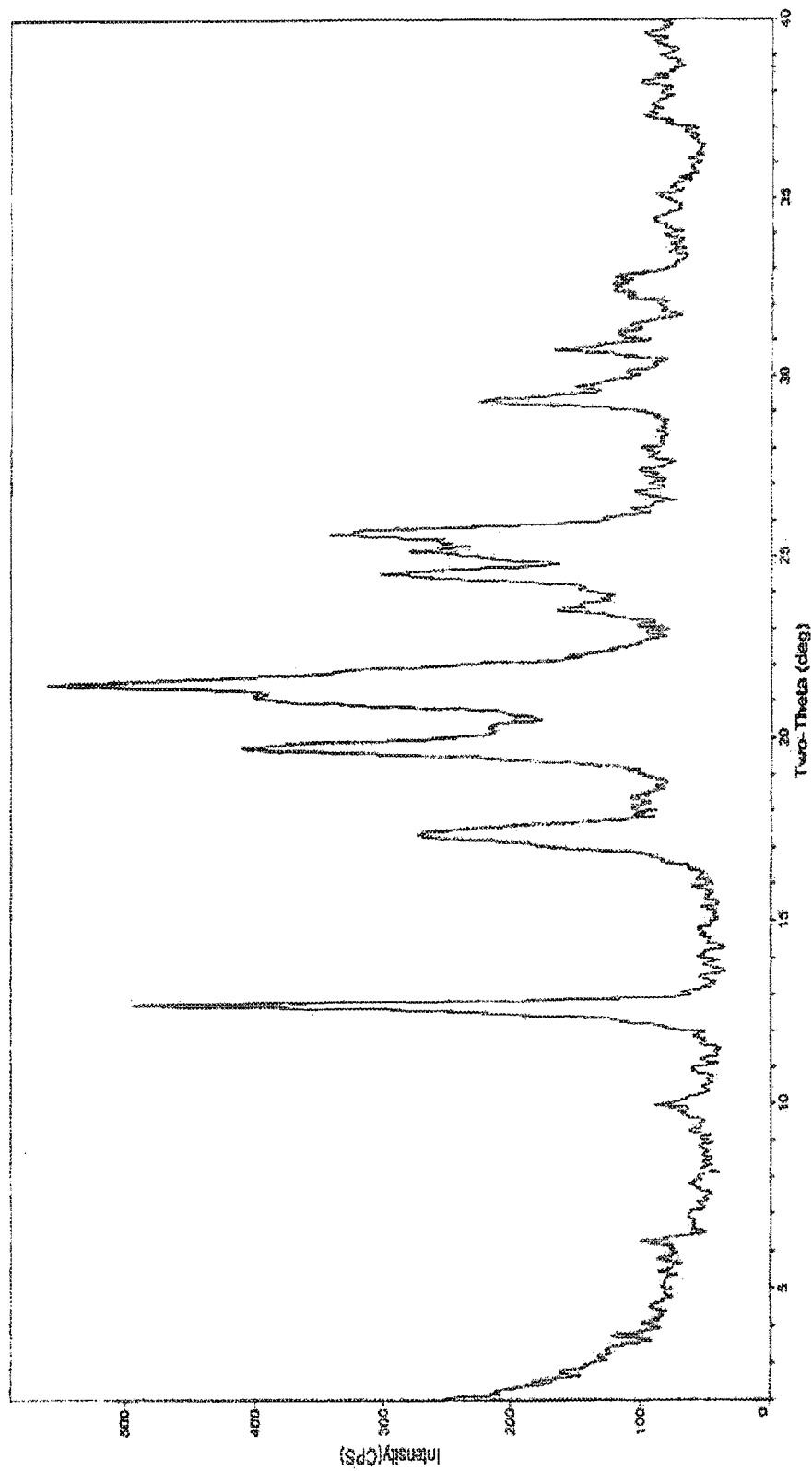

This application is a national phase entry under 35 USC 371 of International Patent Application No.: PCT/IN2014/000718 filed on 13 Nov. 2014, which claims priority from Indian Application No. 3565/MUM/2013 filed on 13 Nov. 2013, the disclosures of which are incorporated in their entirety by reference herein.

FIELD OF THE INVENTION

The field of the invention relates to processes for the preparation of lorcaserin and pharmaceutically acceptable salts, solvates and hydrates thereof. The invention also relates to stable crystalline Form I of lorcaserin hydrochloride and processes for its preparation.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Lorcaserin hydrochloride is an agonist of the $5\text{-}HT_{2c}$ receptor and shows effectiveness at reducing obesity in animal models and humans developed by Arena Pharmaceuticals. It is chemically represented as (R)-8-chloro-1-methyl-2,3,4,5-tetrahydro-1H-3-benzazepine hydrochloride having Formula (I) as depicted herein below.

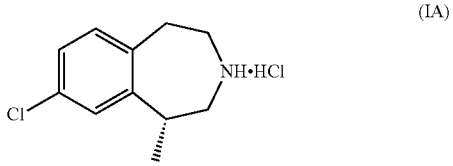

U.S. Pat. No. 6,953,787 B2 discloses compound of Formula (I) and pharmaceutically acceptable salt, solvates or hydrates thereof and process for preparation thereof.

U.S. Pat. No. 8,168,624 B2 discloses (R)-8-chloro-1-methyl-2,3,4,5-tetrahydro-1H-3-benzazepine hydrochloride hemihydrate and process for its preparation. The patent also discloses crystalline Form I, Form II and Form III of (R)-8-chloro-1-methyl-2,3,4,5-tetrahydro-1H-3-benzazepine hydrochloride. The crystalline Form I and Form II are reported as anhydrous, non-solvated crystal forms. The crystalline Form III displays a dehydration feature calculated as a 3.7% weight loss which is consistent with the theoretical weight loss of 3.7% for a hemihydrate.

The patent discloses that anhydrous Form I and Form II readily converts to a hemihydrate, upon exposure to moisture. The dynamic vapor sorption (DVS) data for each of the three crystal forms reveals the hygroscopic nature of both Forms I and II, which readily adsorb moisture at relative humidity (RH) greater than about 40-60%. In addition, both Forms I and II were calculated to adsorb about 3.8% moisture between about 40 and about 80% RH which is consistent with conversion to the hemihydrate (Form III).

X-ray powder diffraction (XRPD) carried out on both Forms I and II after the DVS cycle confirmed this conversion. In contrast, the DVS data in connection with Form III shows that it is substantially non-hygroscopic, adsorbing less than 0.5% water at 90% RH and the XRPD pattern showed no change in crystalline form after the DVS cycle.

International (PCT) Publication Nos. WO 2003/086306 A1, WO 2005/019179 A1, WO 2006/069363 A1, WO 2007/120517 A1, WO 2008/070111 A1 and WO 2009/111004 A1 discloses various synthetic approaches for the preparation of (R)-8-chloro-1-methyl-2,3,4,5-tetrahydro-1H-3-benzazepine, its related salts, enantiomers, crystalline forms and intermediates.

International (PCT) Publication No. WO 2006/071740 A1 discloses combination of (R)-8-chloro-1-methyl-2,3,4,5-tetrahydro-1H-3-benzazepine with other agents.

International (PCT) Publication No. WO 2012/030938 A1 discloses various salts of lorcaserin with optically active acids.

U.S. PG-Pub No. US 2014/0187538 A1 discloses amorphous lorcaserin hydrochloride and amorphous solid dispersion comprising lorcaserin hydrochloride and one or more pharmaceutically acceptable carriers and processes for their preparation.

International (PCT) Publication No. WO 2014/135545 A1 discloses solid dispersion comprising amorphous lorcaserin hydrochloride and one or more pharmaceutically acceptable water soluble polymers.

SUMMARY OF THE INVENTION

In one general aspect, there is provided a stable crystalline Form I of lorcaserin hydrochloride of Formula (IA).

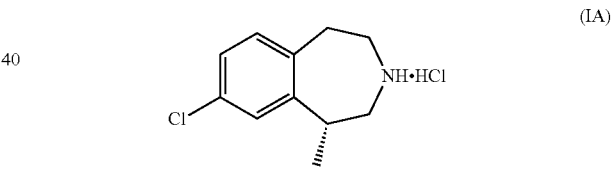

In another general aspect, there is provided a process for the preparation of stable crystalline Form I of lorcaserin hydrochloride.

In another general aspect, there is provided a process for the preparation of (R)-8-chloro-1-methyl-2,3,4,5-tetrahydro-1H-3-benzazepine of Formula (I) and pharmaceutically acceptable salts thereof,

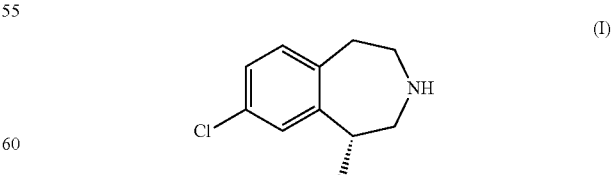

the process comprising:

(a) reacting 4-chlorophenyl acetic acid (VI) or its reactive derivative with a compound of Formula (V) or its salts to prepare a compound of Formula (IV),

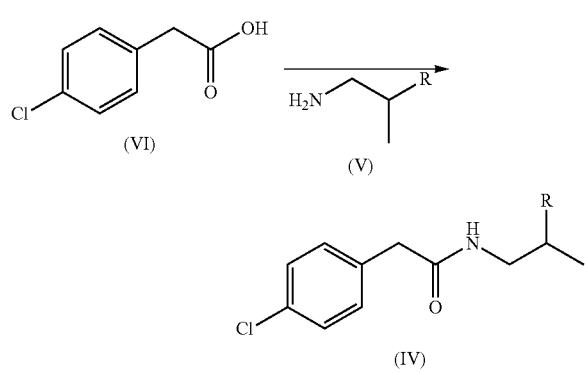

(VI) → (V) → (IV)

wherein R is halogen (Cl, Br, I), OH, O—$C_1$-$C_6$-alkyl, O—$C_1$-$C_6$-alkylaryl, O—CO—$C_1$-$C_6$-alkyl, O—CO-aryl, $OSO_2R'$ and R' is $C_1$-$C_6$-alkyl, aryl, heteroaryl each optionally substituted by one or more halogen, cyano, nitro, $C_1$-$C_4$-alkyl, $C_1$-$C_4$-haloalkyl, $C_1$-$C_4$-alkoxy or $C_1$-$C_4$-haloalkoxy, (b) reducing the compound of Formula (IV) with a reducing agent to obtain a compound of Formula (III) or its salt;

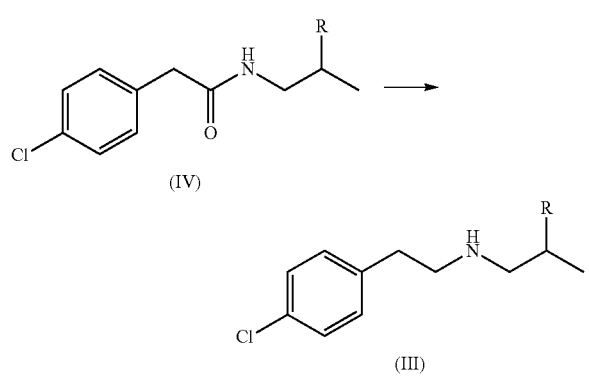

(IV) → (III)

(c) cyclizing the compound of Formula (III) or its salt with a cyclizing reagent to obtain 8-chloro-1-methyl-2,3,4,5-tetrahydro-1H-3-benzazepine of Formula (II);

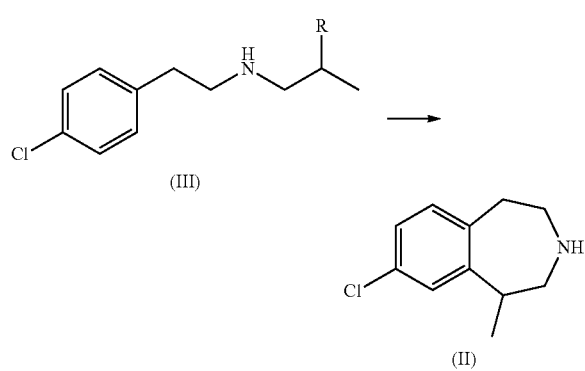

(III) → (II)

(d) reacting 8-chloro-1-methyl-2,3,4,5-tetrahydro-1H-3-benzazepine of Formula (II) with a resolving agent to obtain (R)-8-chloro-1-methyl-2,3,4,5-tetrahydro-1H-3-benzazepine of Formula (I); and

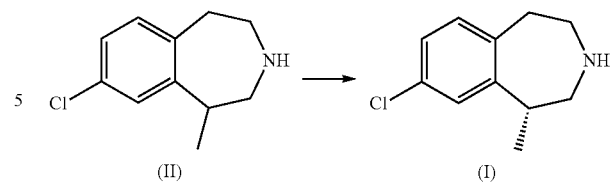

(II) → (I)

(e) optionally, converting (R)-8-chloro-1-methyl-2,3,4,5-tetrahydro-1H-3-benzazepine of Formula (I) into its pharmaceutically acceptable salts.

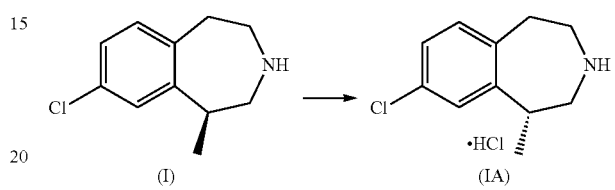

(I) → (IA)

In another general aspect, there is provided a pharmaceutical composition comprising stable crystalline Form I of lorcaserin hydrochloride together with one or more of pharmaceutically acceptable carriers, excipients or diluents.

BRIEF DESCRIPTION OF THE ACCOMPANYING DRAWINGS

FIG. 1. shows an x-ray diffractogram (XRD) of crystalline Form I of lorcaserin hydrochloride as prepared in Example-7.

Figure 2:
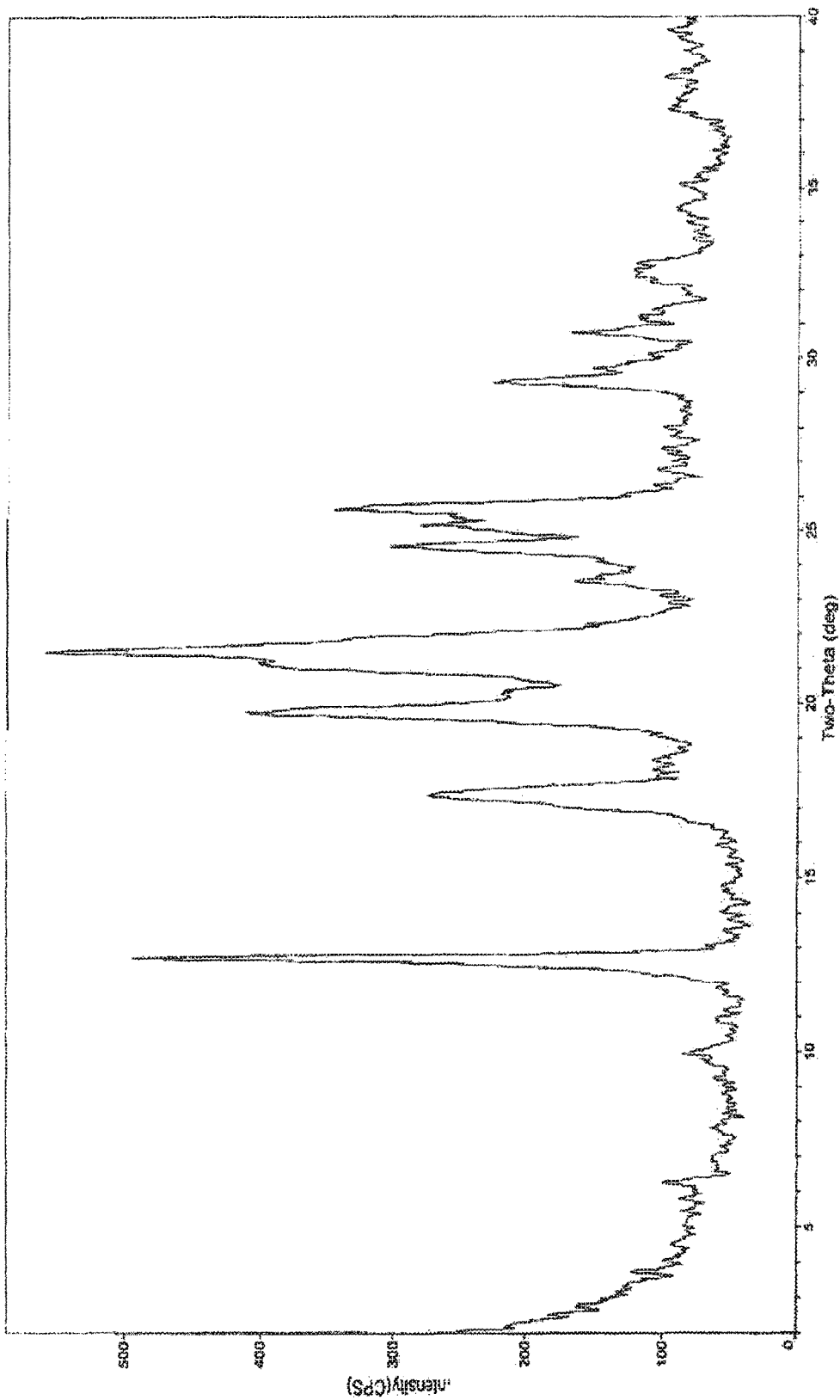

FIG. 2. shows an x-ray diffractogram (XRD) of crystalline Form I of lorcaserin hydrochloride as prepared in Example-9.

Figure 3:
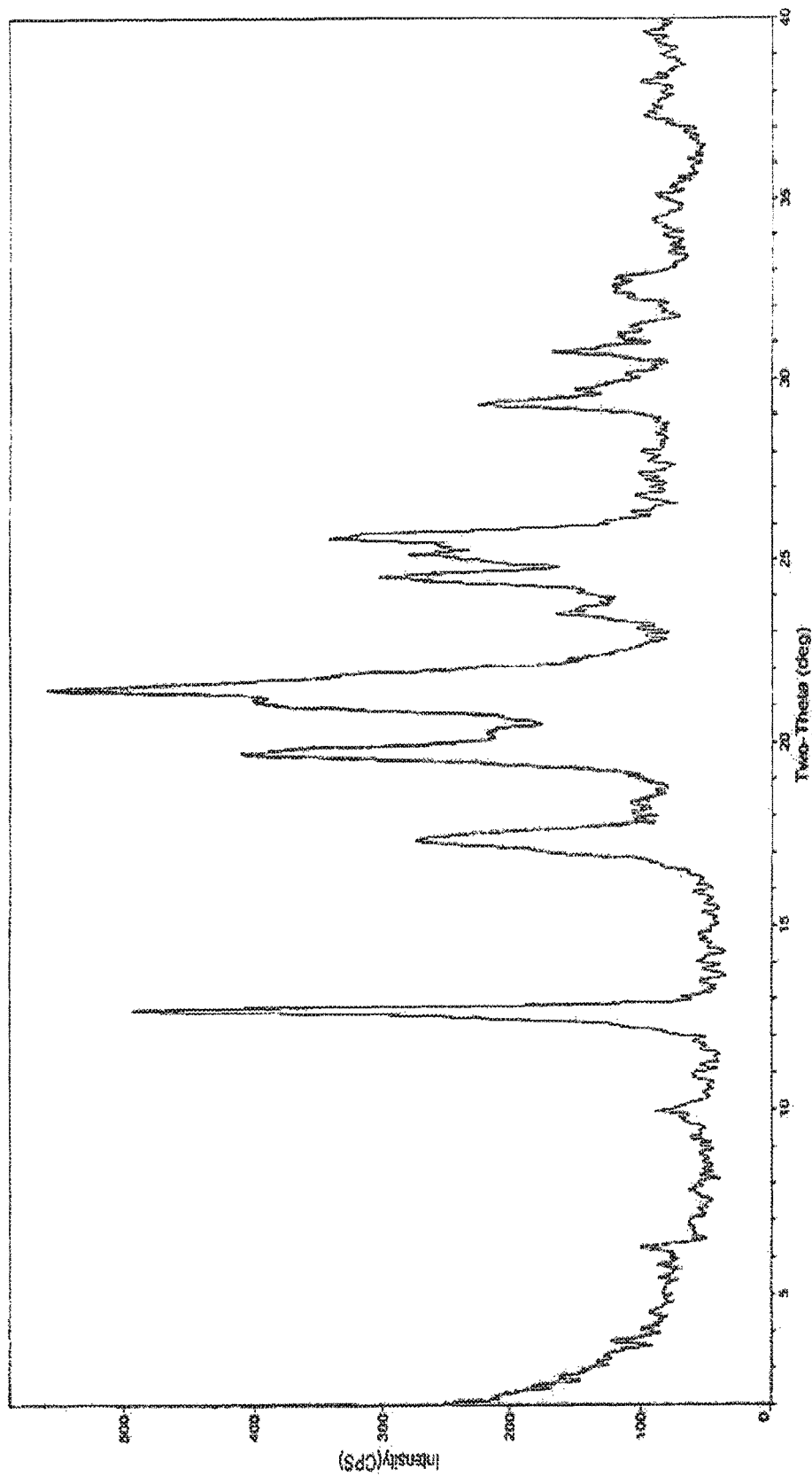

FIG. 3. shows an x-ray diffractogram (XRD) of stable crystalline Form I of lorcaserin hydrochloride.

DETAILED DESCRIPTION OF THE INVENTION

The above and other objects of the present invention are achieved by the process of the present invention, which leads to a stable crystalline Form I of lorcaserin hydrochloride suitable for pharmaceutical preparations and having greater stability. The invention also provides a process for the preparation of a stable crystalline Form I of lorcaserin hydrochloride.

All ranges recited herein include the endpoints, including those that recite a range "between" two values. Terms such as "about", "general", and "substantially" are to be construed as modifying a term or value such that it is not an absolute. This includes, at very least, the degree of expected experimental error, technique error and instrument error for a given technique used to measure a value.

As used herein, the term "stable" includes crystalline Form I of lorcaserin hydrochloride that does not convert to any other solid form when stored at a temperature of up to about 40° C. and at a relative humidity of about 25% to about 75% up to about three months or more.

As used herein, the terms "substantially free" means crystalline Form I containing 0.5% or less of any other solid forms. In particular, crystalline Form I containing 0.3% or less, 0.2% or less, 0.1% or less or not in detectable amount of any other solid forms when measured by X-ray powder diffraction.

As used herein, the terms "obtaining" means isolating the crystalline Form I of lorcaserin hydrochloride by way of filtration, filtration under vacuum, centrifugation, decantation. The product obtained may be further or additionally dried to achieve the desired moisture values. For example, the product may be dried in a tray drier, dried under vacuum and/or in a Fluid Bed Drier.

As used herein the term "pharmaceutically acceptable salts" refers to salts prepared by using inorganic or organic acids, for example hydrochloride, hydrobromide, hydrogen sulfate, phosphate etc. that are listed in the Journal of Pharmaceutical Science, 66, 2 (1977) and incorporated herein by reference.

In one general aspect, there is provided a stable crystalline Form I of lorcaserin hydrochloride of Formula (IA).

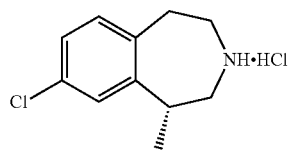

(IA)

In general, the stable crystalline Form I of lorcaserin hydrochloride has an X-ray powder diffraction pattern having characteristic peaks expressed in degrees 2θ (±0.2°) at 6.4, 10.1, 12.8, 17.4, 19.7, 20.4, 21.2, 23.6, 24.5, 25.2, 25.8, 29.4, 30.8 and 32.5±0.2 2θ.

In general, the stable crystalline Form I of lorcaserin hydrochloride has a moisture content that is less than 0.5% w/w.

The prior art discloses that crystalline Form I of lorcaserin hydrochloride readily absorbs moisture at RH greater than about 40-60% RH. The calculated moisture absorbed by anhydrous crystalline Form I is about 3.8% which relates to a hemihydrate Form III.

The present invention provides a process for the preparation of a stable crystalline Form I of lorcaserin hydrochloride, wherein the obtained crystalline Form I does not convert to a hemihydrate form when stored and packed under special conditions of the present invention.

The crystalline Form I of lorcaserin hydrochloride having less than 0.5% water as manufactured by the process of the present invention was subjected to stability for at least 3 months at 25° C./60% RH or at about 40° C./75% RH. The stability conditions and the results are summarized in the following Table-1 and Table-2:

TABLE 1

| Packaging conditions | Packed in a LDPE bag purged with nitrogen and closed with a heat seal, second Black LDPE bag containing a desiccant closed with a twist and tie and enclosed within a triple aluminate pouch containing a desiccant and kept in a small HDPE drum | | | |
|---|---|---|---|---|
| Storage | 25° C. ± 2° C./60% ± 5% RH and 40° C. ± 2° C./75% ± 5% RH | | | |

| Sr. No. | Test | Specification | 1 Month | 2 Months | 3 Months |
|---|---|---|---|---|---|
| 1. | Description | White to off-white | off-white | off-white | off-white |
| 2. | X-Ray Diffraction | The X-ray diffractogram should confirm the Form-I | Form I | Form I | Form I |
| 3. | Water (%) | Less than 0.5% w/w | 0.31% | 0.35% | 0.35% |

TABLE 2

| Packaging conditions | Packed in a LDPE bag purged with nitrogen and closed with a twist and tie, second Black LDPE bag containing a desiccant and closed with a twist and tie and enclosed within a triple aluminate pouch containing a desiccant and kept in a small HDPE drum | | | |
|---|---|---|---|---|
| Storage | 25° C. ± 2° C./60% ± 5% RH and 40° C. ± 2° C./75% ± 5% RH | | | |

| Sr. No. | Test | Specification | 1 Month | 2 Months | 3 Months |
|---|---|---|---|---|---|
| 1. | Description | White to off-white | off-white | off-white | off-white |
| 2. | X-Ray Diffraction | The X-ray diffractogram should confirm the Form-I | Form I | Form I | Form I |
| 3. | Water (%) | Less than 0.5% w/w | 0.31% | 0.35% | 0.35% |

In a further aspect, the stable crystalline Form I of lorcaserin hydrochloride can be stored under nitrogen atmosphere and packed in a double polythene bag which is either heat sealed or twisted and tied with a thread (primary packing). The primary packing containing the crystalline Form I of lorcaserin hydrochloride can be kept inside a black color polyethylene bag containing a desiccant (molecular sieves) which is either heat sealed or twisted and tied, and the above double polyethylene bags may further be placed inside a triple laminated bag, optionally containing a desiccant which is either heat sealed or twisted and tied. Finally, the triple laminated bag can be kept inside a closed high density polyethylene (HDPE) container and stored in a controlled environment chamber at 25° C. and/or 40° C.

In another general aspect, there is provided a stable crystalline Form I of lorcaserin hydrochloride substantially free of any other solid forms. In particular, the stable crystalline Form I of lorcaserin hydrochloride contains 0.5% or less of any other solid forms.

In another general aspect, there is provided a process for the preparation of crystalline Form I of lorcaserin hydrochloride of Formula (IA),

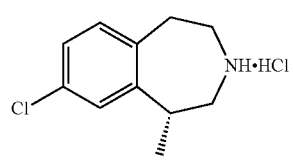

(IA)

the process comprising:
(a) treating lorcaserin acid addition salt with a base in one or more solvents;
(b) removing the solvent to obtain lorcaserin base;
(c) treating the lorcaserin base with a hydrochloride source in one or more solvents to obtain lorcaserin hydrochloride; and
(d) drying the lorcaserin hydrochloride at 70° C. or above to obtain the crystalline Form I of lorcaserin hydrochloride.

In general, the lorcaserin acid addition salt comprises one or more of D- and L-tartaric acid, diacetyltartaric acid, dibenzoyltartaric acid, mandelic acid, malic acid, lactic acid, camphorsulfonic acids, alpha-methylbenzylamine (e.g. S and R forms or diastereomerically pure forms), norephedrine, 2-phenylglycinol, ephedrine, N-methylephedrine, cyclohexylethylamine, 1,2-diaminocyclohexane, camphoric acid, α-methoxy-α-trifluoromethylphenyl acetic acid (MTPA or Mosher's acid), pyrrolidone-5-carboxylic acid, di-O-isopropylene-keto-glutamic acid, di-toluoyl tartaric acid, camphoric acid, or ketogulonic acid. In particular, D- and L-tartaric acid may be used.

In general, the base may include one or more of sodium hydroxide, potassium hydroxide, lithium hydroxide, calcium hydroxide, sodium carbonate, potassium carbonate, sodium bicarbonate, or potassium bicarbonate. In particular, sodium hydroxide may be used.

The solvents which may be used at step (a) include one or more of water, alcohols selected from methanol, ethanol, isopropanol, 1-butanol and t-butanol; esters selected from ethyl acetate, propyl acetate, isopropyl acetate and butyl acetate; chlorinated solvents selected from methylene dichloride, ethylene dichloride, and chloroform and mixture thereof. In particular, a mixture of water and methylene dichloride may be used. The reaction can be carried out at a temperature range from about 25° C. to about 90° C.

The hydrochloride source may be selected from HCl (g), conc. hydrochloric acid, IPA-HCl, ethyl acetate-HCl, and acetone-HCl solutions. In particular, HCl (g) may be used.

The solvents may be removed by any of the known methods, for example distillation, distillation under vacuum, decantation, centrifugation and evaporation. In particular, distillation under vacuum may be used to obtain lorcaserin base.

The solvents at step (c) may include one or more of alcohols selected from methanol, ethanol, isopropanol, 1-butanol and t-butanol; esters selected from ethyl acetate, propyl acetate, isopropyl acetate and butyl acetate; chlorinated solvents selected from methylene dichloride, ethylene dichloride, and chloroform or mixtures thereof. In particular, ethyl acetate may be used.

In general, the lorcaserin base obtained at step (b) is treated with a HCl (g) in ethyl acetate at about 0° C. to about 15° C. to obtain a pH of about 1.5-2.5. The reaction mixture thus obtained may be stirred for about 30 minutes at about 30° C. to 40° C. to obtain lorcaserin hydrochloride. The lorcaserin hydrochloride thus obtained may be initially dried for 2 hours at 50° C. to 55° C. and then at above 70° C. for about 15-20 hours to obtain the crystalline Form I of lorcaserin hydrochloride having water content less than 0.5%. In particular, the drying is done at about 90° C. to about 110° C.

In another general aspect, there is provided a process for the preparation of a crystalline Form I of lorcaserin hydrochloride. The process includes treating lorcaserin hydrochloride hemihydrate Form III with one or more of excipients and drying the lorcaserin hydrochloride at 70° C. or above to obtain the stable crystalline Form I of lorcaserin hydrochloride.

In general, the excipients which may be used include a polymer selected from methacrylic acid copolymers, polyvinylpyrrolidone (PVP), 4-vinylpyrrolidone-vinyl acetate copolymer (copovidone) or copolymers of methacrylic acid and ethylacrylate (EUDRAGIT® L100-55), hydroxypropylmethyl cellulose acetate succinate (HPMC-AS), or hydroxypropylmethyl cellulose (HPMC). The polyvinylpyrrolidone (PVP) of different grades selected from K-15, K-30, K-60, K-90 and K-120 may be used: In particular, hydroxypropylmethyl cellulose (HPMC) may be used for the preparation of stable crystalline Form I of lorcaserin hydrochloride.

In another general aspect, there is provided a process for the preparation of (R)-8-chloro-1-methyl-2,3,4,5-tetrahydro-1H-3-benzazepine of Formula (I) and pharmaceutically acceptable salts thereof (IA),

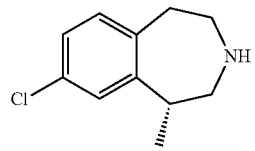

(I)

the process comprising:
(a) reacting 4-chlorophenyl acetic acid (VI) or its reactive derivative with a compound of Formula (V) or its salts to prepare a compound of Formula (IV),

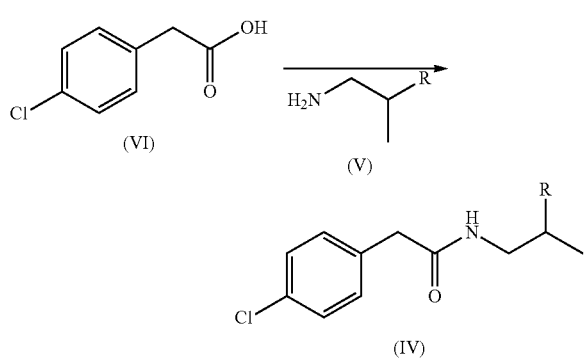

wherein R is halogen (Cl, Br, I), OH, O—$C_1$-$C_6$-alkyl, O—$C_1$-$C_6$-alkylaryl, O—CO—$C_1$-$C_6$-alkyl, O—CO-aryl, $OSO_2R'$ and R' is $C_1$-$C_6$-alkyl, aryl, heteroaryl each optionally substituted by one or more halogen, cyano, nitro, $C_1$-$C_4$-alkyl, $C_1$-$C_4$-haloalkyl, $C_1$-$C_4$-alkoxy or $C_1$-$C_4$-haloalkoxy;
(b) reducing the compound of Formula (IV) with a reducing agent to obtain a compound of Formula (III) or its salt;

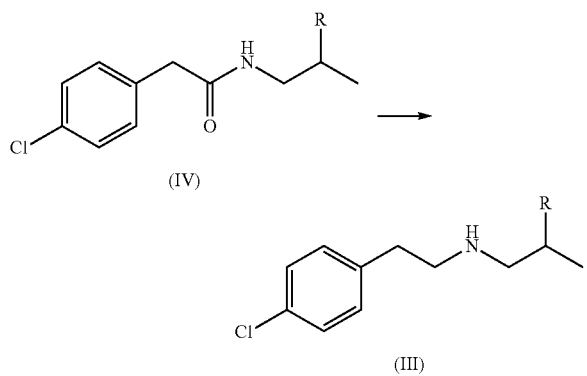

(c) cyclizing the compound of Formula (III) or its salt with a cyclizing reagent to obtain 8-chloro-1-methyl-2,3,4,5-tetrahydro-1H-3-benzazepine of Formula (II);

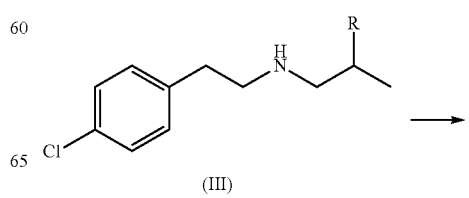

-continued

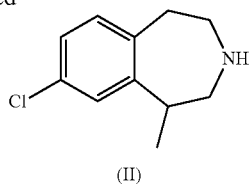

(II)

(d) reacting the 8-chloro-1-methyl-2,3,4,5-tetrahydro-1H-3-benzazepine of Formula (II) with a resolving agent to obtain (R)-8-chloro-1-methyl-2,3,4,5-tetrahydro-1H-3-benzazepine of Formula (I); and

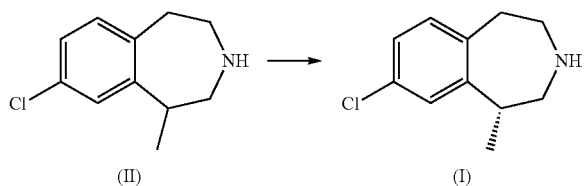

(e) optionally, converting the (R)-8-chloro-1-methyl-2,3,4,5-tetrahydro-1H-3-benzazepine of Formula (I) into its pharmaceutically acceptable salts.

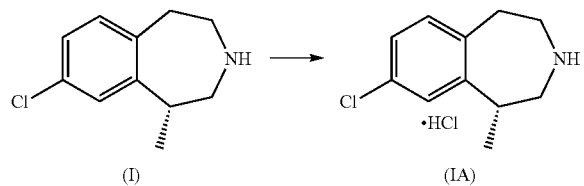

In general, the 4-chlorophenylacetic acid of Formula (VI) or its reactive derivative (for example, a mixed acid anhydride, an acid halide or an ester) is reacted with a compound of Formula (V) or its salts wherein R is OH, halogen (Cl, Br, I), O—$C_1$-$C_6$-alkyl, O—$C_1$-$C_6$-alkylaryl, O—CO—$C_1$-$C_6$-alkyl, O—CO-aryl, $OSO_2R'$ and R' is $C_1$-$C_6$-alkyl, aryl, heteroaryl each optionally substituted by one or more halo, cyano, nitro, $C_1$-$C_4$-alkyl, $C_1$-$C_4$-haloalkyl, $C_1$-$C_4$-alkoxy or $C_1$-$C_4$-haloalkoxy to obtain compound of Formula (IV). The R is preferably selected from Cl, Br, I.

The reaction is carried out in the presence of one or more solvents selected from methylene dichloride, ethylene dichloride, carbon tetrachloride, toluene, benzene, ethylbenzene and xylene or a mixture thereof and at temperature ranges from between 0° C. to 80° C.

In general, the reducing agent comprises one or more $NaBH_4$, $NaBH_3CN$, combination of iodine and aluminum hydrides selected from $LiAlH_4$, $C_1$-$C_8$-alkyl aluminum hydrides, $C_2$-$C_{16}$-dialkyl aluminum hydrides, Red-Al, monoalkoxy or dialkoxy or trialkoxy aluminum hydrides in combination with $AlCl_3$, boranes selected from $BH_3$ or $B_2H_6$, $BH_3$:$CH_3SCH_3$, $BH_3$:triethylamine, $BH_3$:diethyl ether, $BH_3$:tetrahydrofuran, $C_1$-$C_8$alkyl boranes, $C_2$-$C_{16}$dialkyl boranes, $C_3$-$C_{24}$trialkyl boranes or cyclic boranes, or $BF_3$-etharate and $NaBH_4$.

Due to potential sensitivity of the reducing agents to air, the reaction is conducted under an inert atmosphere, e.g. under nitrogen atmosphere.

The reaction can be carried out using any inert solvent, for example dialkyl ether or cyclic ether (e.g., THF) or hydrocarbons or mixtures thereof at temperature selected from between 30° C. to 90° C. The duration of the reduction can be carried out for any amount of time till the completion of the reaction.

In general, the cyclizing reagent which may be used include a reagent that can be used in a reaction to cyclize a linear or branched molecule or portion of a molecule. In general, the cyclizing reagent, includes one or more of $BF_3$, $BF_3$:TBME, $BF_3$:$OEt_3$, $AlCl_3$, $AlBr_3$, $C_1$-$C_8$-alkylaluminum halide selected from methyl aluminum chloride, ethyl aluminum chloride, $C_2$-$C_{16}$-dialkylaluminum halide selected from dimethyl aluminum chloride, diethyl aluminum chloride, trialkyl aluminum, sulfuric acid, $CF_3SO_3H$, $CH_3SO_3H$, p-toluene sulfonic acid, phosphoric acid, polyphosphoric acid, $H_3PO_4$/$P_2O_5$, $FeCl_3$, $TiCl_4$, $ZrCl_4$ and $ZnCl_4$. In particular, $AlCl_3$ may be used.

In general, the cyclization can be carried out in the presence or in the absence of solvents. The solvent includes one or more of decahydronaphthalene, 1,2-dichlorobenzene, methylene dichloride, ethylene dichloride, carbon tetrachloride, toluene, xylene, ethylbenzene or mixture thereof. In particular, 1,2-dichlorobenzene, methylene dichloride and toluene or a mixture thereof may be used.

The cyclization can be carried out at an elevated temperature of about 80° C. to about 170° C. The duration of the reaction can be from about 10 minutes to about 24 hours.

In general, the resolving agent at step (d) refers to reagents that are used for resolution of the racemic mixtures of compounds by one or more of known methods in the art. The resolving agents include one or more of optically active acids e.g. D- and L-tartaric acid, diacetyltartaric acid, dibenzoyltartaric acid, mandelic acid, malic acid, lactic acid, camphorsulfonic acids, alpha-methyl benzylamine (e.g. S and R forms or diastereomerically pure forms), norephedrine, 2-phenylglycinol, ephedrine, N-methylephedrine, cyclohexylethylamine, 1,2-diaminocyclohexane, camphoric acid, α-methoxy-α-trifluoromethylphenyl acetic acid (MTPA or Mosher's acid), pyrrolidone-5-carboxylic acid, di-O-isopropylene-keto-glutamic acid, di-toluoyl tartaric acid, camphoric acid and ketogulonic acid. In particular, D- and L-tartaric acid may be used.

The resolution of the racemic mixture can also be carried out by elution on a column packed with an optically active resolving agent (e.g., dinitrobenzoyl phenylglycine).

The resolution step can be carried out using solvents that include polar solvents or water-miscible solvents. The solvents include one or more of alcohols selected from methanol, ethanol, isopropanol, n-butanol and t-butanol; esters selected from ethyl acetate, propyl acetate, isopropyl acetate, n-butyl acetate, and t-butyl acetate; ethers selected from tetrahydrofuran and 1,4-dioxane; ketones selected from acetone, methyl ethyl ketone, and methyl isobutyl ketone; and water or mixtures thereof. In particular, the mixture of n-butanol and water or mixture of acetone and water or mixture of methyl ethyl ketone or water can be used. The reaction can be carried out at temperature ranges from 25° C. to 90° C. to obtain lorcaserin of Formula (I).

In general, the lorcaserin of Formula (I) may be converted to its pharmaceutically acceptable salts.

In general, the pharmaceutically acceptable salts refers to pharmaceutically acceptable salts prepared by using pharmaceutically acceptable acids including inorganic and organic acids, for example acetic, benzenesulfonic benzoic, citric, camphorsulfonic, ethenesulfonic, dichloroacetic, formic, fumaric, gluconic, glutamic, hipporic, hydrochloric, hydrobromic, hydroiodic, isethionic, lactic, maleic, malic, mandelic, methanesulfonic, mucic, nitric, oxalic, pamoic, pantothenic, phosphoric, succinic, sulfuric, tartaric, oxalic or p-toluenedulfonic acid that are listed in the Journal of Pharmaceutical Science, 66, 2 (1977).

The acid addition salts can be obtained as a direct product of compound synthesis. As an alternative, the free base can be dissolved in one or more solvents containing pharmaceutically acceptable acid, and the salt can be isolated by evaporating the solvent or otherwise separating the salt and solvent.

In another aspect, there is provided a process for the preparation of lorcaserin of Formula (I) and its pharmaceutically acceptable salts, according to the reaction scheme-1 substantially as depicted herein after.

The invention also encompasses pharmaceutical compositions comprising stable crystalline Form I of lorcaserin hydrochloride of the invention. As used herein, the term "pharmaceutical compositions" includes pharmaceutical formulations like tablets, pills, powders, liquids, suspensions, emulsions, granules, capsules, suppositories, or injection preparations.

The pharmaceutical compositions containing the stable crystalline Form I of lorcaserin hydrochloride of the invention may be prepared by using diluents or excipients such as fillers, bulking agents, binders, wetting agents, disintegrating agents, surface active agents, and lubricants. Various modes of administration of the pharmaceutical compositions of the invention can be selected depending on the therapeutic purpose, for example tablets, pills, powders, liquids, suspensions, emulsions, granules, capsules, suppositories, or injection preparations.

In another general aspect, there is provided a pharmaceutical composition comprising stable crystalline Form-I of lorcaserin hydrochloride together with one or more of pharmaceutically acceptable carriers, excipients or diluents.

Having described the invention with reference to certain preferred embodiments, other embodiments, reaction conditions, temperature control and solvent system may become apparent to one skilled in the art from consideration of the examples provided herein after. The examples are provided as one of the possible ways to practice the invention and should not be considered as limitation of the scope of the invention.

EXAMPLES

Example 1

Preparation of 4-chloro-N-(2-hydroxypropyl) benzeneacetamide

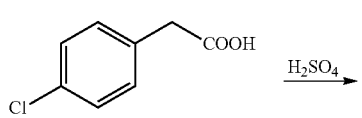

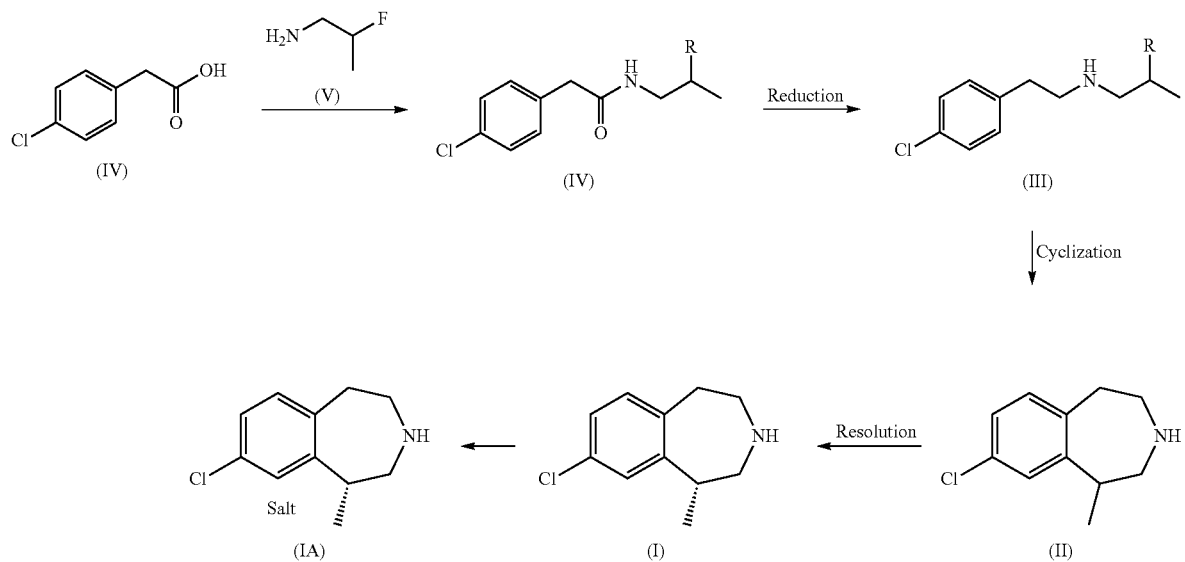

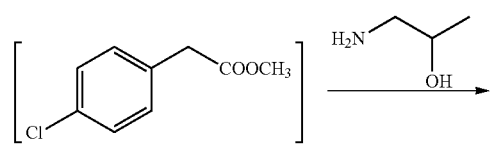

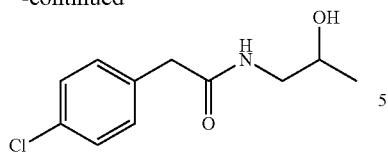

100 g of 4-chloro phenyl acetic acid was taken into a 1.0 liter round bottom flask. 500 ml of methanol and 2.0 ml. con. H₂SO₄ (2.0%) were added. The reaction mixture was heated upto reflux temperature and stirred for 1 hour at 60-66° C. After completion of the reaction, the solvent was distilled out and the reaction mass was cooled to 25-30° C. 151.6 g of 1-amino-2-propanol was added into the reaction mixture, heated and stirred for 5-8 hours at 90° C. The reaction mass was cooled to 40-50° C. 1500 mL water was added into the reaction mass and the reaction mast was cooled to 10-20° C. and stirred for 1 hour at 10-20° C. The product was filtered and washed with 100 ml water and then dried at 45-50° C. for 8 hours. Water content<0.5%; Yield: 85-93%.

Example-2

Preparation of 4-chloro-N-(2-chloropropyl) benzeneacetamide

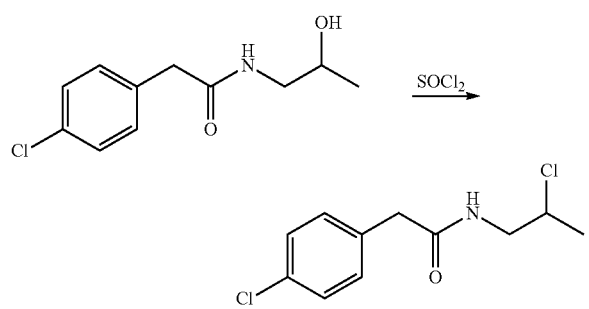

50 g of 4-chloro-N-(2-hydroxypropyl)-benzeneacetamide and 250 ml of toluene were taken into a 500 ml round bottom flask and heated upto 35-40° C. 20 mL of thionyl chloride was added at 35-40° C. The reaction mass was stirred for one hour at 35-40° C. After completion of the reaction, the solvent was distilled out. 60 ml of isopropyl alcohol was added and the reaction mass was heated to 50° C. and then 200 ml water was added into that at 10-15° C. and stirred for one hour at this temperature. The solid obtained was filtered and washed two times with 25 ml of pre-cooled water. The product was dried at 45-50° C. for 6-8 hours.

Example-3

Preparation of 4-chloro-N-(2-chloropropyl) benzeneacetamide

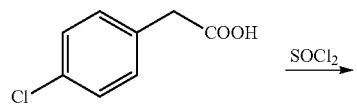

150 g of 4-chloro phenyl acetic acid, 300 ml of methylene dichloride, and 3.75 ml DMF were taken into a 500 ml round bottom flask under nitrogen atmosphere. 77.8 ml of thionyl chloride was added at 25-35° C. The reaction mass was stirred at 25-35° C. till the completion of the reaction. After completion of the reaction, the solvent was distilled out and 75 ml of methylene dichloride was added, stirred and distilled out under vacuum below 45° C. After distillation, 300 mL of methylene dichloride was added and stirred for 10 minutes and kept under nitrogen atmosphere.

278 g of PCl₅ and 300 ml of methylene dichloride were taken in a round bottom flask under nitrogen atmosphere and cooled to 0-5° C. 100.23 g of 1-amino-2-propanol in 300 mL of methylene dichloride was added into that within 1-2 hrs at 0-10° C. under N₂ atm. The reaction mass was stirred for 1-2 hours at 0-10° C. The solvent was removed under vacuum at 0° C. to 30° C. The reaction mass was cooled to 0-5° C. 150 ml of methylene dichloride was added and stirred for 10 min. and solvent was removed under vacuum. 225 ml water was added into the reaction mass. Sodium carbonate solution (566.6 g sodium carbonate in 2250 ml of water) was added. The above prepared solution of acid chloride compound was added into the reaction mass at 0-10° C. and stirred for 30 min at 0-10° C. and then 25-30° C. for 30 min. After completion of the reaction, the solvent was removed under vacuum. The resulting slurry was filtered and washed two times with 75 ml water. Yield: 90-98.1%.

Example-4

Preparation of 2-chloro-N-(4-chlorophenethyl) propanamine

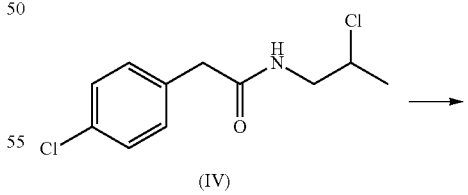

(IV)

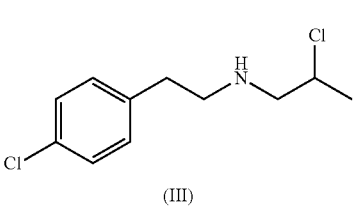

(III)

In a 500 ml of round bottom flask under N₂ atmosphere, 140 ml of THF was taken and cooled to −15 to −20° C. 4.3 g of lithium aluminum hydride was added followed by the addition of 8.43 gm of AlCl₃ and then cooled to −35 to −40° C. A solution of 10.0 g of amide compound in 100 mL of THF was added and stirred for 3-4 hours at −35 to −40° C. After completion of the reaction, sodium hydroxide solution (2.4 g sodium hydroxide in 100 mL of water) was added below 20° C., followed by the addition of 50 ml of toluene and 50 ml of water at 25-30° C. and stirred for 15 min. The reaction mass was filtered through a hyflow bed and washed with 25 ml toluene. The organic layer was distilled out under vacuum. 38 mL of ethyl acetate was added, stirred and filtered. The filtrate was collected and cooled to 0-10° C. Dry HCl gas was passed into the reaction mass till pH 2-4. The product thus obtained was filtered and wash with pre-cooled ethyl acetate.

Example-5

Preparation of 2-chloro-N-(4-chlorophenethyl)propanamine hydrochloride

In a round bottom flask, under N₂ atmosphere, 200 ml of THF was taken at 25 to 30° C. 23.18 g of sodium borohydride was added and cooled to 0 to 5° C. and then 115.36 g of BF₃-etherate was added and the reaction mass was stirred at 0 to 5° C. for 30 minutes. 100 g amide compound dissolved in 300 mL THF was added slowly into the reaction mass at 0-5° C. The reaction mass was stirred for 4-5 hours at 60-65° C. After completion of the reaction, the reaction mass was cooled to 10-20° C. and 20 mL hydrochloric acid was added and stirred for 15 minutes. The solvent was removed under reduced pressure. 200 ml water and 200 ml toluene were added and further 20 mL HCl was added and stirred for 30 minutes at 30-40° C. 350 ml of 20% aqueous sodium hydroxide was added and the pH was adjusted to 11 to 13. The organic and aqueous layers were separated. The organic layer was treated with diluted HCl and pH was adjusted to 2-4 and stirred for 15-30 minutes at 0-20° C. The product was filtered and washed with toluene.

Example-6

Preparation of 8-chloro-1-methyl-2,3,4,5-tetrahydro-1H-3-benzazepine

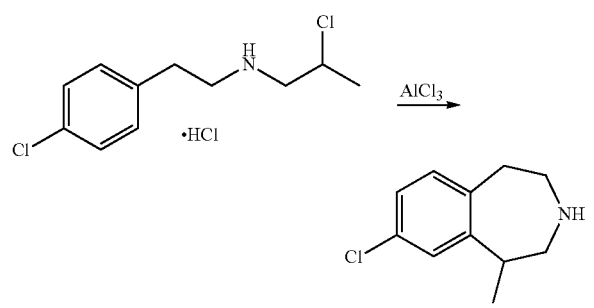

130 g of 2-chloro-N-(4-chlorophenethyl)propanamine and 286 ml of 1,2-dichloro benzene were taken into a round bottom flask under nitrogen atmosphere and stirred for 10 minutes. 161.34 g of anhydrous aluminum chloride was added into the reaction mass and heated upto 120-125° C. The reaction mass was stirred for 2-3 hours. After completion of the reaction, the reaction mass was slowly added into pre-cooled dilute HCl solution and stirred for 15-20 minutes. The two layers were separated and 260 mL methylene dichloride was added into the lower layer and the layers were separated. 325 mL dilute sodium hydroxide solution was added into the methylene dichloride layer for alkaline pH. The lower organic layer was separated and after charcoal treatment the solvent was removed under vacuum. 390 mL ethyl acetate and 130 ml water was added into the reaction mass. 65 ml dilute sodium hydroxide solution was added and stirred for 15 minutes. The layers were separated and the solvent was removed under vacuum to get the product. Yield: 95-99%.

Example-7

Preparation of Crystalline Form I of Lorcaserin Hydrochloride

In a round bottom flask, 560 g of methyl ethyl ketone and 40 ml water were taken and 100 g of 8-chloro-1-methyl-2,3,4,5-tetrahydro-1H-3-benzazepine was added and stirred for 10 minutes. The reaction mass heated to 55 to 60° C. and 19.3 g of L-(+)-tartaric acid was added slowly and stirred for one to two hours. The reaction mass was further stirred at 10-15° C. for an hour and the product was filtered and washed with a mixture of methyl ethyl ketone and water. The wet cake and 150 ml methyl ethyl ketone were taken in another flask and heated to 75-80° C. 20-25 ml water was added and stirred for an hour. Further, the reaction mass was stirred for an hour at 0-5° C. The product was filtered and washed with methyl ethyl ketone.

100 g tartrate salt of 8-chloro-1-methyl-2,3,4,5-tetrahydro-1H-3-benzazepine and 300 mL water were taken in another round bottom flask. 200 mL methylene dichloride was added and the reaction mass was cooled to 10-20° C. 17.2 g sodium hydroxide dissolved in 89 ml water was added into the reaction mass at 10-20° C. The reaction mass was stirred for an hour at 25-30° C. and the layers were separated. The solvent was removed from the organic layer under vacuum and then 100 mL ethyl acetate was added into that and distilled out. Further, 100 mL ethyl acetate was added and stirred for 15 minutes. The reaction mass was filtered through a hyflow bed and the filtrate was treated with dry HCl gas till a pH of 1.5 to 2.5 was obtained at 0-10° C. and it was stirred for about 30 minutes to an hour. The product was then filtered and washed with ethyl acetate and then dried in a vacuum oven at 50° C. to 55° C. for 2 hours. The product was further dried at 90° C. to 110° C. for 20 hours to obtain crystalline Form I of lorcaserin hydrochloride. Yield: 87.5-98.6%.

Example-8

Preparation of Crystalline Form I of Lorcaserin Hydrochloride

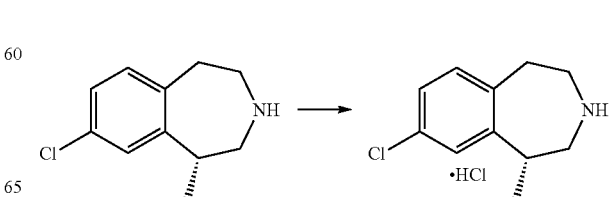

In a round bottom flask, 2.20 g lorcaserin, 30 mL methylene chloride, 17.4 mL of 1M HCl in ether were added and the mixture was stirred for 5-15 minutes at room temperature. The solvent was removed under reduced pressure to give a white solid. This solid was again dissolved in 30 ml methylene chloride, 17.4 mL of 1M HCl solution and stirred for 5-15 minutes at room temperature. The solvent was removed under reduced pressure to give lorcaserin hydrochloride. The product was dried in a vacuum oven at 50° C. to 55° C. for 2 hours. The product was further dried at 90° C. to 110° C. for 20 hours to obtain crystalline Form I of lorcaserin hydrochloride.

Example-9

Preparation of Crystalline Form I Lorcaserin Hydrochloride 50 g of lorcaserin hydrochloride hemihydrate and 50 g of hydroxypropylmethyl cellulose (HPMC) 3CPC were mixed in a blender at 25° C. to 35° C. The mixture was mixed for 30 minutes and unloaded. The solid thus obtained was dried in a vacuum oven at 50° C. to 55° C. for 2 hours. The product was further dried at 90° C. to 110° C. for 20 hours to obtain crystalline Form I of lorcaserin hydrochloride.

While the present invention has been described in terms of its specific embodiments, certain modifications and equivalents will be apparent to those skilled in the art and intended to be included within the scope of the invention.

We claim:

1. A stable crystalline Form I of lorcaserin hydrochloride wherein the crystalline Form I of lorcaserin hydrochloride does not convert to any other solid form when stored at a temperature of up to about 40° C. and at a relative humidity of about 25% to about 75% up to about three months or more.

2. The stable crystalline Form I of lorcaserin hydrochloride according to claim 1 has an X-ray powder diffraction pattern having characteristic having peaks expressed in degrees 2θ (±0.2°) at 6.4, 10.1, 12.8, 17.4, 19.7, 20.4, 21.2, 23.6, 24.5, 25.2, 25.8, 29.4, 30.8 and 32.5±0.2 2θ.

3. The stable crystalline Form I of lorcaserin hydrochloride according to claim 1, wherein the lorcaserin hydrochloride has a moisture content that is less than 0.5% w/w.

4. A stable crystalline Form I of lorcaserin hydrochloride, wherein the crystalline Form I of lorcaserin hydrochloride does not convert to any other solid form when stored at a temperature of up to about 40° C. and at a relative humidity of about 25% to about 75% up to about three months or more when stored under nitrogen atmosphere and packed in a primary packing containing a double polythene bag which is either heat sealed or twisted and tied with a thread, keeping the primary packing containing the crystalline Form I of lorcaserin hydrochloride inside a black color polyethylene bag containing a desiccant which is either heat sealed or twisted and tied, placing the double polyethylene bag inside a triple laminated bag, optionally containing a desiccant which is either heat sealed or twisted and tied, and placing the triple laminated bag inside a closed high density polyethylene (HDPE) container and storing in a controlled environment chamber at 25° C. and/or 40° C.

5. The stable crystalline Form I of lorcaserin hydrochloride according to claim 1, substantially free of any other solid forms.

6. The stable crystalline Form I of lorcaserin hydrochloride according to claim 5 contains 0.5% or less of any other solid forms.

7. A process for the preparation of crystalline Form I of lorcaserin hydrochloride according to claim 1, the process comprising:
(a) treating lorcaserin acid addition salt with a base in one or more solvents;
(b) removing the solvent to obtain lorcaserin base;
(c) treating the lorcaserin base with a hydrochloride source in one or more solvents to obtain lorcaserin hydrochloride; and
(d) drying the lorcaserin hydrochloride at 70° C. or above to obtain the crystalline Form I of lorcaserin hydrochloride.

8. The process according to claim 7, wherein the base comprises one or more of sodium hydroxide, potassium hydroxide, lithium hydroxide, calcium hydroxide, sodium carbonate, potassium carbonate, sodium bicarbonate, or potassium bicarbonate.

9. The process according to claim 7, wherein the solvent comprises one or more of alcohols selected from methanol, ethanol, isopropanol, 1-butanol and t-butanol; esters selected from ethyl acetate, propyl acetate, isopropyl acetate and butyl acetate; chlorinated solvents selected from methylene dichloride, ethylene dichloride, and chloroform, or mixtures thereof.

10. The process according to claim 7, wherein the hydrochloride source is selected from HCl (g), conc. hydrochloric acid, IPA-HCl, ethyl acetate-HCl, or acetone-HCl.

11. The process according to claim 7, wherein the drying is done at about 90° C. to about 110° C.

12. A process for the preparation of stable crystalline Form I of lorcaserin hydrochloride, the process comprising treating lorcaserin hydrochloride hemihydrate Form III with one or more of excipients and drying the lorcaserin hydrochloride at 70° C. or above to obtain the stable crystalline Form I of lorcaserin hydrochloride.

13. The process according to claim 12, wherein the excipients comprise a polymer selected from methacrylic acid copolymers, polyvinylpyrrolidone (PVP), 4-vinylpyrrolidone-vinyl acetate copolymer (copovidone) or copolymers of methacrylic acid and ethylatrylate (EUDRAGIT® L100-55), hydroxypropylmethyl cellulose acetate succinate (HPMC-AS), or hydroxypropylmethyl cellulose (HPMC).

14. A process for the preparation of (R)-8-chloro-1-methyl-2,3,4,5-tetrahydro-1H-3-benzazepine of Formula (I) and pharmaceutically acceptable salts thereof (IA),

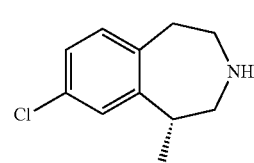

(I)

the process comprising:
(a) reacting 4-chlorophenyl acetic acid (VI) or its reactive derivative with a compound of Formula (V) or its salts to prepare a compound of Formula (IV),

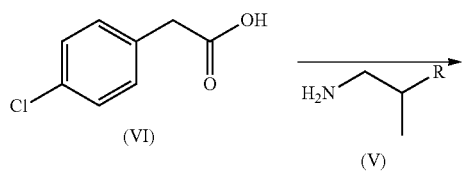

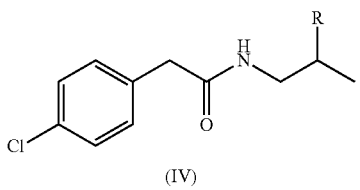

(IV)

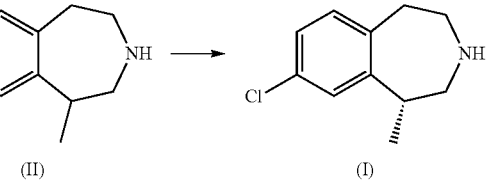

wherein R is halogen (Cl, Br, I), OH, O—$C_1$-$C_6$-alkylaryl, O—CO—$C_1$-$C_6$-alkyl, O—CO-aryl, or $OSO_2R'$ and R' is $C_1$-$C_6$-alkyl, aryl, heteroaryl each optionally substituted by one or more halogen, cyano, nitro, $C_1$-$C_4$-alkyl, $C_1$-$C_4$-haloalkyl, $C_1$-$C_4$-alkoxy or $C_1$-$C_4$-haloalkoxy;

(b) reducing the compound of Formula (IV) with a reducing agent to obtain a compound of Formula (III) or its salt;

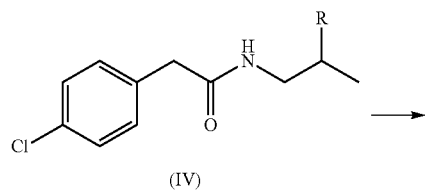

(c) cyclizing the compound of Formula (III) or its salt with a cyclizing reagent to obtain 8-chloro-1-methyl-2,3,4,5-tetrahydro-1H-3-benzazepine of Formula (II);

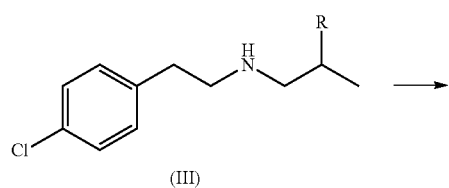

(d) reacting the 8-chloro-1-methyl-2,3,4,5-tetrahydro-1H-3-benzazepine of Formula (II) with a resolving agent to obtain (R)-8-chloro-1-methyl-2,3,4,5-tetrahydro-1H-benzazepine of Formula (I); and (e) optionally, converting the (R)-8-chloro-1-methyl-2,3,4,5-tetrahydro-1H-3-benzazepine of Formula (I) into its pharmaceutically acceptable salts,

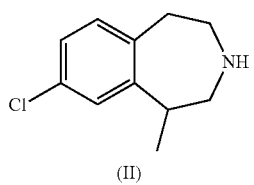

15. The process according to claim 14, wherein the reaction at step (a) is carried out in the presence of one or more solvents selected from methylene dichloride, ethylene dichloride, carbon tetrachloride, toluene, benzene, ethylbenzene and xylene, or mixtures thereof.

16. The process according to claim 14, wherein the reducing agent comprises one or more $NaBH_4$, $NaBH_3CN$, combination of iodine and aluminum hydrides selected from $LiAlH_4$, $C_1$-$C_8$-alkyl aluminum hydrides, $C_2$-$C_{16}$-dialkyl aluminum hydrides, Red-Al, monoalkoxy or dialkoxy or trialkoxy aluminum hydrides in combination with $AlCl_3$, boranes selected from $BH_3$ or $B_2H_6$, $BH_3$:$CH_3SCH_3$, $BH_3$:triethylamine, $BH_3$:diethyl ether, $BH_3$:tetrahydrofuran, $C_1$-$C_8$-alkyl boranes, $C_2$-$C_{16}$-dialkyl boranes, $C_3$-$C_{24}$-trialkyl boranes or cyclic boranes, or $BF_3$-etharate and $NaBH_4$.

17. The process according to claim 14, wherein the cyclizing agent includes one or more of $BF_3$, $BF_3$:TBME, $BF_3$:$OEt_3$, $AlCl_3$, $AlBr_3$, $C_1$-$C_8$-alkylaluminum halide selected from methyl aluminum chloride, ethyl aluminum chloride, $C_2$-$C_{16}$-dialkylaluminum halide selected from dimethyl aluminum chloride, diethyl aluminum chloride, trialkyl aluminum, sulfuric acid, $CF_3SO_3H$, $CH_3SO_3H$, p-toluene sulfonic acid, phosphoric acid, polyphosphoric acid, $H_3PO_4/P_2O_5$, $FeCl_3$, $TiCl_4$, $ZrCl_4$ and $ZnCl_4$.

18. The process according to claim 14, wherein the cyclization is carried out in the presence or in the absence of solvents.

19. The process according to claim 14, wherein the resolving agent comprises one or more of optically active acids selected from D- and L-tartaric acid, diacetyltartaric acid, dibenzoyltartaric acid, mandelic acid, malic acid, lactic acid, camphorsulfonic acids, alpha-methyl benzylamine (S and R forms or diastereomerically pure forms), norephedrine, 2-phenylglycinol, ephedrine, N-methylephedrine, cyclohexylethylamine, 1,2,diaminocyclohexane, camphoric acid, α-methoxy-α-trifluoromethylphenyl acetic acid (MTPA or Mosher's acid), pyrrolidone-5-carboxylic acid, di-O-isopropylene-keto-glutamic acid, di-toluoyl tartaric acid, camphoric acid and ketogulonic acid.

20. A pharmaceutical composition comprising stable crystalline Form I of lorcaserin hydrochloride according to claim 1 having one or more of pharmaceutically acceptable carriers, excipients or diluents.

* * * * *